United States Patent [19]
Root et al.

[11] Patent Number: 6,013,007
[45] Date of Patent: Jan. 11, 2000

[54] ATHLETE'S GPS-BASED PERFORMANCE MONITOR

[75] Inventors: Gary Miller Root, San Francisco; Frank van Hoorn, Mill Valley, both of Calif.

[73] Assignee: Liquid Spark, LLC, San Francisco, Calif.

[21] Appl. No.: 09/048,214

[22] Filed: Mar. 26, 1998

[51] Int. Cl.[7] .................................................. G01B 21/00
[52] U.S. Cl. .............................. 482/8; 482/900; 482/902; 701/213
[58] Field of Search ........................... 482/1–9, 900–902; 701/213–216; 342/357

[56] References Cited

U.S. PATENT DOCUMENTS

| | | | |
|---|---|---|---|
| 5,148,002 | 9/1992 | Kuo et al. | 219/211 |
| 5,592,401 | 1/1997 | Krammer | 702/153 |
| 5,757,929 | 5/1998 | Wang et al. | 381/300 |
| 5,825,327 | 10/1998 | Krasner | 342/357 |

*Primary Examiner*—Glenn E. Richman
*Attorney, Agent, or Firm*—Sughrue, Mion, Zinn, Macpeak & Seas, PLLC

[57] ABSTRACT

A Global Positioning System (GPS) based personal athletic performance monitor for providing an athlete with real-time athletic performance feedback data such as elapsed exercise time, distance covered, average pace, elevation difference, distance to go and/or advice for reaching pre-set targets. The monitor is integrated with an AM/FM/TV personal radio, and the athletic performance feedback is provided through a set of audio headphones using an audio module. The monitor can be connected to an external personal computer via a serial or infrared port for further data storage and long term trend analysis, or to a remote computer via modem, where historical performance data is collected and logically compiled from participating athletes worldwide. Results are then transferred to an Internet web site which displays comparison data representing the relative performances of two or more athletes, provides customized individual training advice and virtual competitions, and an opportunity for advertisers to reach highly well defined potential customers. Geographically and demographically targeted advertising messages are also downloaded to the performance monitor while connected to the remote computer.

38 Claims, 11 Drawing Sheets

PREFERRED EMBODIMENT DEVICE CONFIGURATION MENUS

Fig. 11

PREFERRED EMBODIMENT DATA STORED FOR PC AND INTERNET USAGE

Fig. 12

ATHLETE'S GPS-BASED PERFORMANCE MONITOR

BACKGROUND OF THE INVENTION

1. Field of the Invention

This invention relates to the application of Global Positioning System (GPS) technology for the personal performance monitoring of outdoor athletes, such as runners, bicyclists, hikers, walkers, skaters, skiers, and so forth, and providing the athlete with real-time performance feedback and optional long-term trend analysis.

2. Background Art

Running, bicycling, and other outdoor sports are becoming increasingly popular as more information about their health benefits becomes available. In order to improve over time, it is important to be able to accurately measure one's performance and progress. Using runners by way of example, this can presently only be done indoors on treadmills. Treadmills provide the runner with continuous readouts of time, distance, speed, pace, inclination, calories burned, and so forth. Outdoors, the runner is limited to wristwatches with built-in stop watches, heart rate monitors, or pedometers.

The development of the Global Positioning System (GPS) by the United States Department of Defense has greatly enhanced one's ability to navigate. Currently, a constellation of high altitude GPS satellites are in orbit and available to provide continuous worldwide position fixes in all types of weather conditions. With the use of GPS receivers, the radio wave signals can be received and used to calculate the current latitude and longitude position coordinates at the receiving location. This system is currently achieving recognition as the superior position locator system for providing accurate worldwide fixes. GPS technology is becoming widely available. New applications, such as dashboard mounted GPS in automobiles are being introduced. Hand held GPS devices are presently on the market for boating, fishing, and hunting. These devices are generally limited to navigation uses only. A visual display is used to show current geographic location, destinations, and navigation instructions for travelling to a selected location. These units are not, however, designed for use by an outdoor athlete. They do not include real-time athletic performance algorithms, audible presentation of information, a means for storing historical exercise session data, or a means for entertaining the athlete. The housings are bulky and typically incorporate built-in GPS antennas, preventing one's ability to conveniently carry the devices while exercising without blocking some or all of the satellite signals. The exclusively visual means of conveying information employed by current devices requires frequent visual interaction, compromising the safety and concentration of the user, making them incompatible with exercise activities.

Thus, there exists a need for a portable GPS unit that is small and light enough to be carried or worn by an outdoor athlete which incorporates real-time athletic performance algorithms for continuously monitoring the athlete's progress and reporting his/her progress periodically during the exercise session. Real-time audio reports would assist and motivate the athlete to improve his/her performance without any visual distractions. An integrated radio can provide the athlete with entertainment.

SUMMARY OF THE INVENTION

Objects of the present invention are:

(1) To provide a device which is portable, rugged, weather resistant, and self-contained;

(2) To provide a device which continuously and accurately determines the position of an outdoor athlete anywhere in the world;

(3) To provide a device which continuously and consistently provides accurate, real-time performance feedback such as elapsed time, elapsed distance, current and average speeds and paces, current climbing rate, and so forth, independent of its outdoor location in the world;

(4) To provide a device which can make real-time recommendations to the athlete on how his/her pre-set performance targets can be achieved;

(5) To provide a device which can optionally continuously monitor the athlete's vital signs such as heart rate and body temperature and can issue warnings based on these measurements as compared to built in limits;

(6) To provide a device which communicates with the athlete through audio signals, thus reducing visual distractions and allowing for safely obtaining performance feedback along poorly illuminated tracks and trails, improving the safety of the athlete;

(7) To provide a device which usefully combines the audio presentation of real-time performance information with music for entertaining the athlete during his/her exercise session;

(8) To provide a device which can store performance data and communicate this data with a personal computer for further storage and long term analysis;

(9) To provide a device which can guide the athlete along a predetermined, unmarked course based on a set of downloaded geographic waypoints;

(10) To provide a device which includes an internal modem for transmitting exercise results to an Internet website where such data is also collected from other participating athletes;

(11) To provide a system by which advertisers can present geographically and demographically targeted messages to a highly well defined group of potential customers;

(12) To provide a device which stimulates and motivates the athlete during an exercise session, resulting in a documented improvement of athletic performance and health over time;

(13) To provide a device which eliminates user assumptions or estimates required by presently available rudimentary devices, such as pedometers; and (14) To provide a device which provides performance data, which is accurate, thorough, and consistent enough to be useful for scientific and medical research on the long term effects of exercise on health.

The above objects and others are accomplished by providing a portable feedback system providing regular updates on an athlete's performance, comprising:

- a global positioning system GPS receiver for obtaining a series of time-stamped waypoints;
- means for computing athletic performance feedback data from the series of time-stamped waypoints obtained by said GPS receiver; and
- means for presenting the athletic performance feedback data to an athlete.

Also provided is a system for comparing an athlete's performance with the performance of other athletes, said system comprising:

a global positioning system GPS receiver for obtaining a series of time-stamped waypoints;

means for computing athletic performance feedback data from the series of time-stamped waypoints obtained by said GPS receiver;

means for presenting the athletic performance feedback data to an athlete; and a modem for transmitting the athletic performance feedback data to a remote computer for comparison with athletic performance feedback data of other athletes.

The monitor can also be used as a health monitoring and analysis tool.

BRIEF DESCRIPTION OF THE DRAWING FIGURES

The invention is best understood with reference to the attached drawings, in which.

DETAILED DESCRIPTION OF THE PREFERRED EMBODIMENTS

Preferred embodiments of the invention are described below with reference to the accompanying drawings.

Figures 1A, 1B:
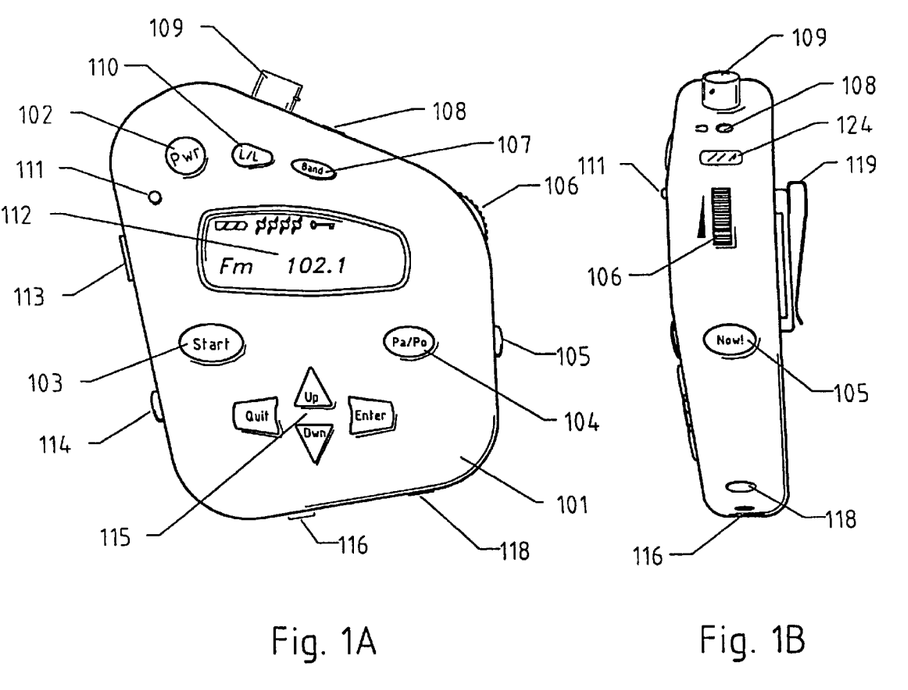
FIGS. 1A and 1B are front and side views, respectively, of a GPS-based personal performance monitor and feedback device according to an embodiment of the invention.
Figure 1C:
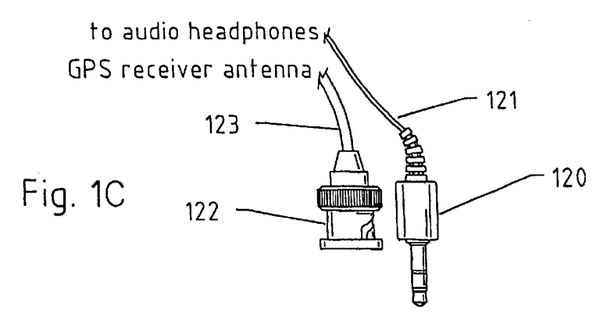
FIG. 1C shows a GPS receiver antenna plug and an audio headphone plug for connection to the GPS-based personal performance monitor and feedback device.

A preferred embodiment of the present invention is shown in FIG. 1A (front view) and FIG. 1B (side view), and FIG. 1C (antenna and audio headphone plugs).

The GPS-based personal performance monitor and feedback device 101 includes input buttons 115 to set the athlete's personal data and preferences, as well as for inputting the feedback options and targets. Device options, GPS initialization status, GPS signal strength, button lock status, pause condition status, menu items, radio band and frequency selection, battery life indicators, performance feedback data, course navigational direction indicators, and latest geographic position are optionally shown on the display 112. A GPS receiver antenna 301 (described below) is plugged into connector 109 using a plug 122, and a set of audio headphones 202 (described below) is plugged into connector 108 using a plug 120 (see FIG. 1C). Button 102 turns the personal performance monitor and feedback device 101 on and commences the initialization process, which consists of acquiring the minimum number of required satellite signals needed to determine the device's initial geographic position. An LED status indicator 111 provides an intuitive visual indicator of device initialization. The LED 111 glows red while the GPS-based personal performance monitor and feedback device is initializing. The LED 111 glows green once the device has automatically initialized and is ready to begin monitoring an exercise session.

A lock/light button 110 disengages certain input buttons, locking the programmed settings, thus preventing accidental changes of these settings. A pause/position button 104 temporarily pauses collection of performance data or, if held for a longer period of time (such as 2 seconds) temporarily replaces the radio band and frequency indicator on display 112 with the latitude and longitude of last updated geographical position. The "Now!" button 105 initiates immediate, updated feedback cycle of the latest measures of athletic performance. In addition to audio performance feedback, measures of athletic performance are simultaneously scrolled on the display 112 during each feedback cycle.

With band selection button 107, a selection between AM, FM, and TV radio bands can be made. While the preferred embodiment of the GPS-based personal performance monitor and feedback device includes an AM/FM/TV radio, it should be appreciated that other audio entertainment systems or combinations of audio systems may be combined with the device, such as an audio cassette tape or audio compact disk player.

The volume thumb wheel 106 controls the volume of the output to the set of audio headphones 202. Atmospheric pressure is measured by a barometric pressure sensor 610 (see FIG. 6) such as those found in current altitude sensing devices for hiking, bicycling, mountaineering, and skydiving. A serial-type connector 118 or an infrared-type port 124 allows for connecting the GPS-based personal performance monitor and feedback device 101 to a personal computer 701 (see FIG. 7) for uploading of historical performance statistics and downloading of geographic waypoints and user device preferences.

Alternatively, an RJ-11-type telephone port 113 allows for connecting the personal performance monitor and feedback device 101 via a telephone line to a remote computer 801 (see FIG. 8) for uploading of performance statistics and downloading of advertising messages. A button 114 automatically connects a modem 613 (see FIG. 6) to the remote computer 801 for data exchange. A connector 116 allows for connection of an external power source.

Figure 2:
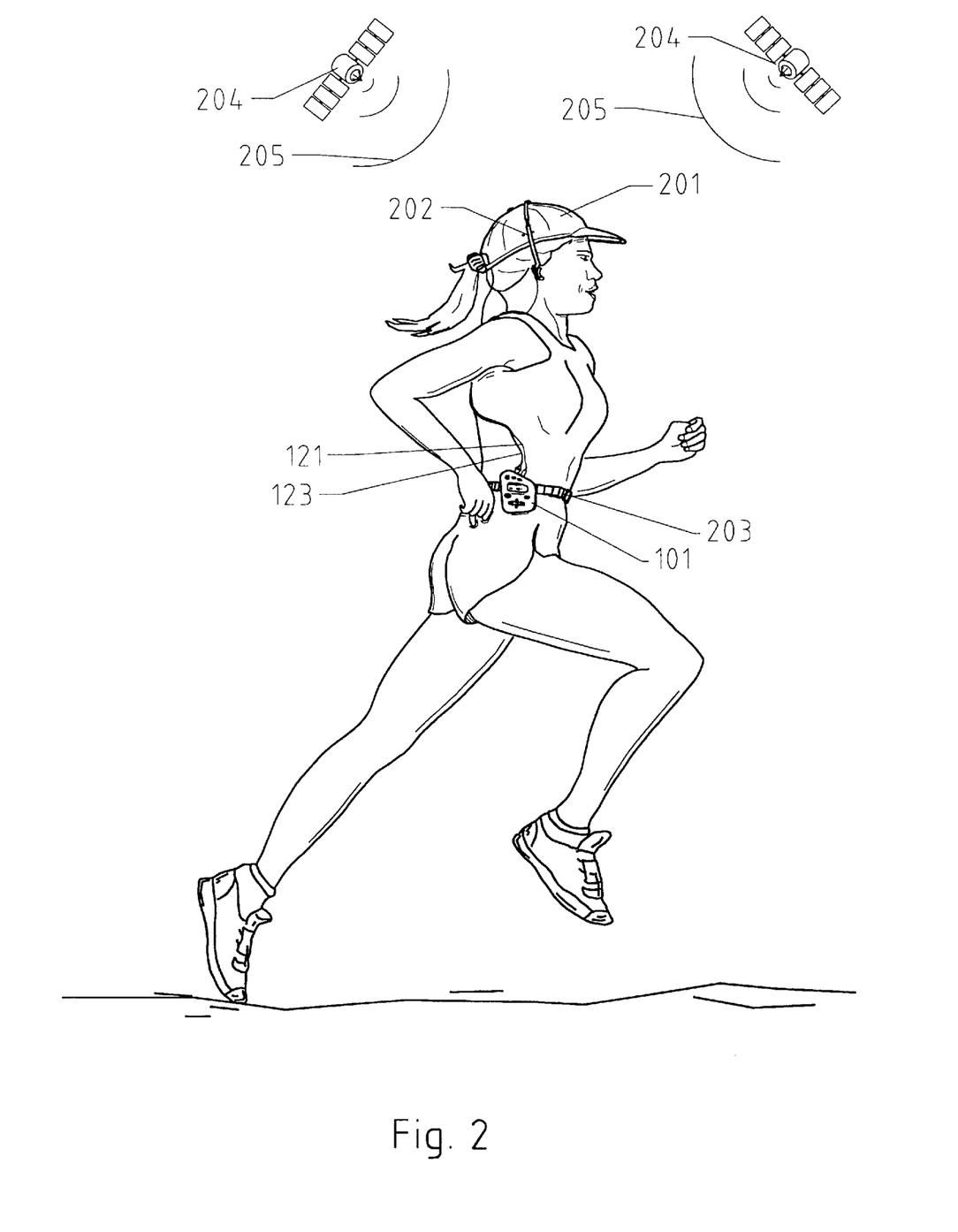
FIG. 2 shows a runner wearing the GPS-based personal performance monitor and feedback device on her waist band, together with a set of audio headphones and a baseball cap outfitted with an internal GPS receiver antenna.
Figure 3:
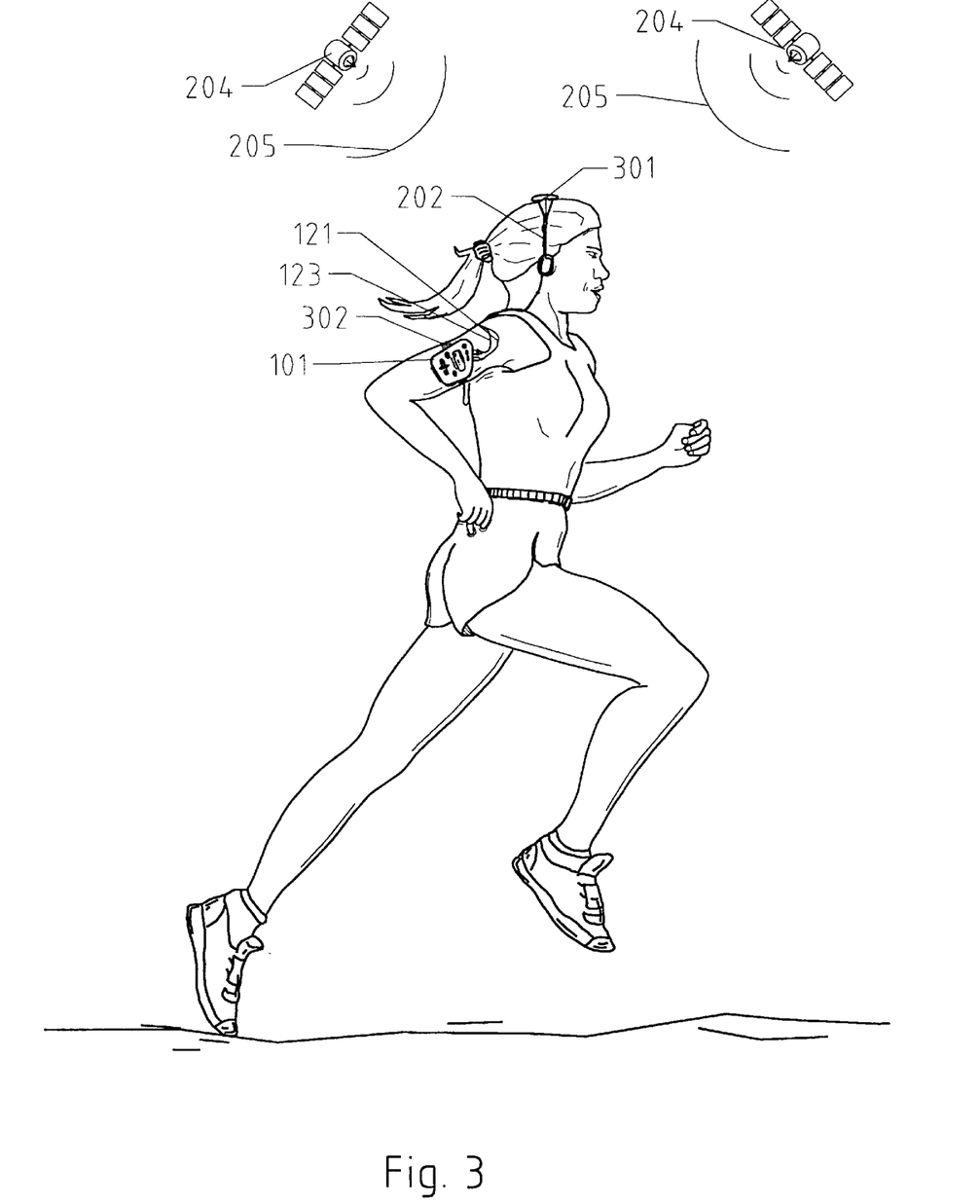
FIG. 3 shows a runner wearing the GPS-based personal performance monitor and feedback device on her upper arm, together with a set of audio headphones having a GPS receiver antenna mounted on top.

The unit 101 can be hooked to an athlete's belt or waistband 203 with a clip 119 (FIG. 1B) as shown in FIG. 2, strapped around the upper arm with a strap 302 as shown in FIG. 3, or simply held by the athlete.

Figures 4, 5:
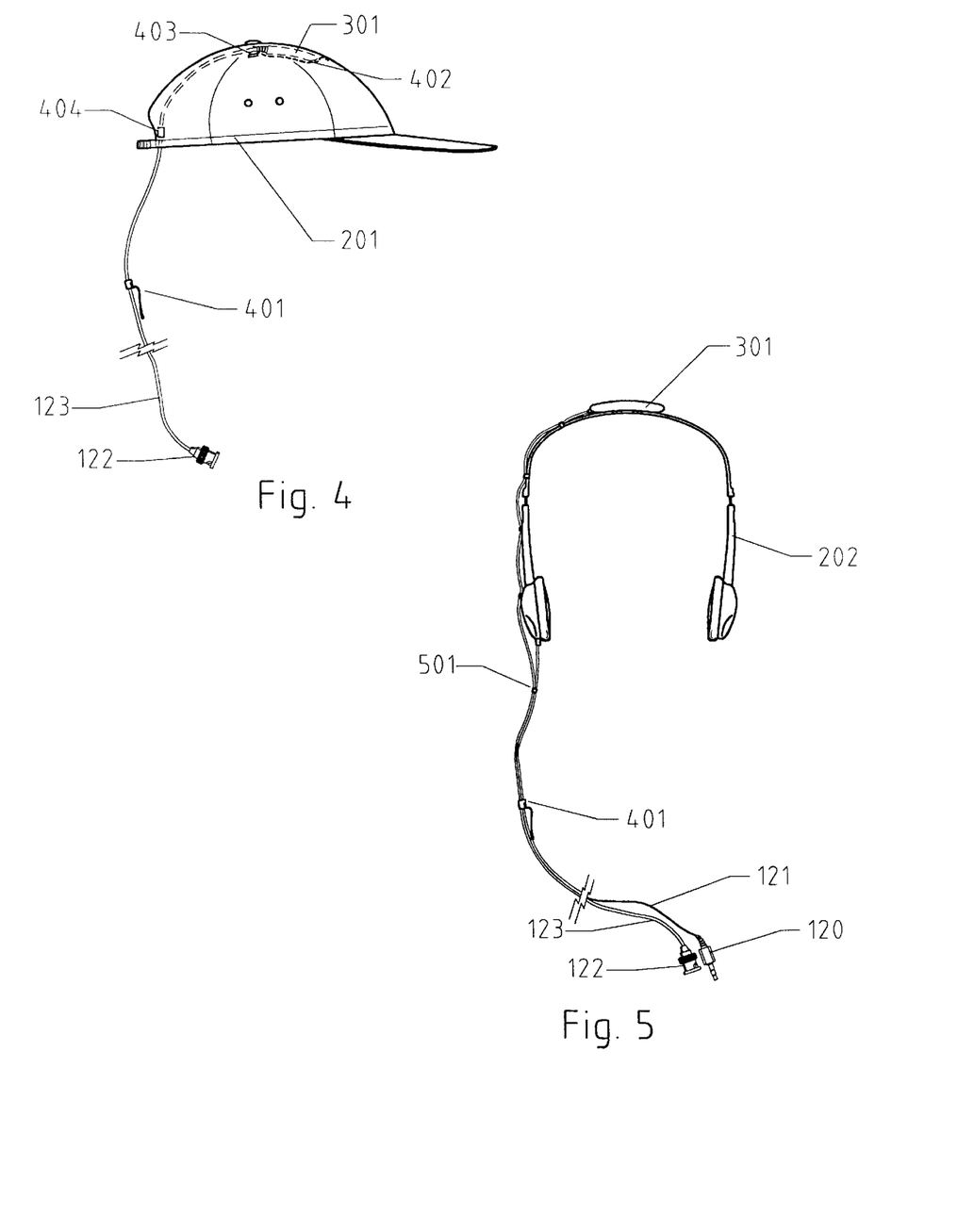
FIG. 4 is a side view of the baseball cap outfitted with the internal GPS receiver antenna.
FIG. 5 is a front view of the set of audio headphones having the GPS receiver antenna mounted on top.

A set of audio headphones 202 (FIG. 2) is worn as usual, along with a baseball cap 201 (FIG. 4). The baseball cap 201 is outfitted with an internal GPS receiver antenna 301.

Alternatively, depending on the athlete's preference, a set of headphones 202 (FIGS. 3 and 5) with the external GPS receiver antenna 301 mounted on top can be worn.

As shown in FIG. 4, an antenna holder (such as a padded pocket) 402 can be sewn into the top of the baseball cap 201. A quick closure 403, such as a VELCRO fastener, locks the GPS receiver antenna 301 in place. The antenna wire 123 (electrical lead to the GPS receiver antenna 301 see FIG. 1C) is guided to the back of the cap and anchored near the bottom edge, such as by using a VELCRO fastener 404.

A clip 401 is used to hook the wire 123 to the athlete's shirt collar, thus redirecting the weight of the wire 123 from the baseball cap 201 to the athlete's shirt.

As shown in FIG. 5, the GPS receiver antenna 301 can be fixed on top of the headband of the set of audio headphones 202. The GPS antenna wire 123 (electrical lead to the GPS receiver antenna 301) is bundled with the headphone wire 121 (electrical lead to the AM/FM/TV radio see FIG. 1C, such as by using a VELCRO fastener 501. A clip 401 is used to hook the wires 123 and 121 to the athlete's shirt collar, thus redirecting the weight of the wires 123 and 121 from the audio headphones 202 to the athlete's shirt.

The athlete's head generally provides a stable, unobstructed platform for the GPS receiver antenna 301, with clear 360 degree exposure to the satellites 204 overhead. Other locations on the user may also provide a suitably stable, unobstructed platform for the GPS receiver antenna 301.

Figure 6:
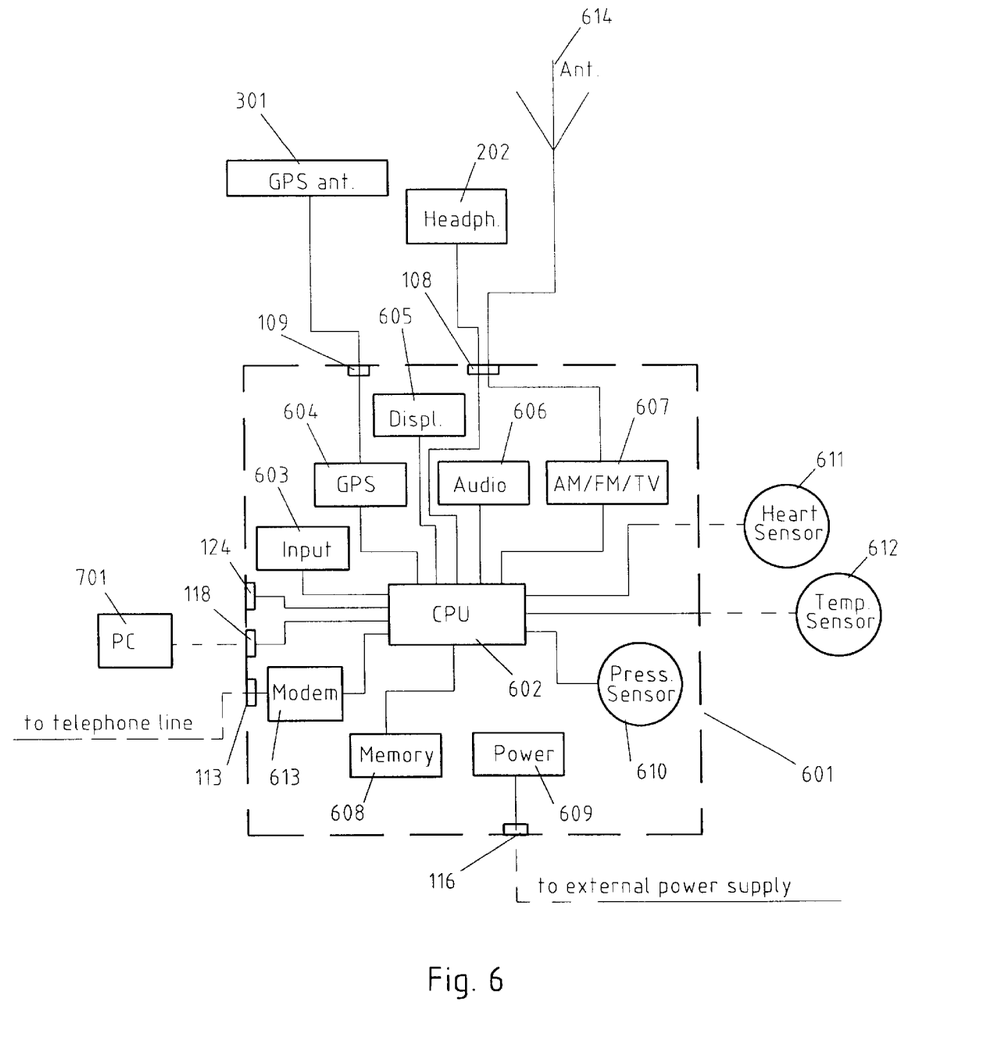
FIG. 6 is a schematic of the electronic components of the GPS-based personal performance and feedback device of the embodiment.

FIG. 6 is an electrical schematic of the internal circuitry of an embodiment of the GPS based performance monitor 101 of the present invention. Inside the housing 601 (shown schematically by a broken line) is a central processor unit 602 (CPU). This CPU controls the operation of the device. Connected to the CPU 602 is a GPS receiver module 604 such as those manufactured by SiRF Technology, Trimble Navigation Limited, and others, an AM/FM/TV radio module 607, an audio module 606, memory 608, input controls 603, a barometric pressure sensor 610, a display 605, a heart rate sensor 611 (optional), a body temperature sensor 612 (optional), a modem 613, a serial-type port 118, an infrared-type port 124, and an external personal computer 701 (optional). The GPS module 604 is connected to a GPS receiver antenna 301. The audio module 606, which can be an amplifier connected to a voice/speech synthesizer, a micro controller generating audio output using a series of stored compressed digital audio files, or some combination of these, is connected to the audio headphones 202 via the CPU 602. The AM/FM/TV radio module 607 is connected to a radio antenna 614 (usually built into the antenna wire lead 121 or the audio headphones 202), and also to the audio headphones 202 via the CPU 602. The device is energized by either an internal power source 609 (such as disposable or rechargeable battery or batteries, e.g., one or more AA or AAA batteries) during exercise sessions or an external power source (such as an AC/DC transformer 704, connected to the device via an electrical lead plugged into connector 116) during uploading and downloading activities.

Figure 7:
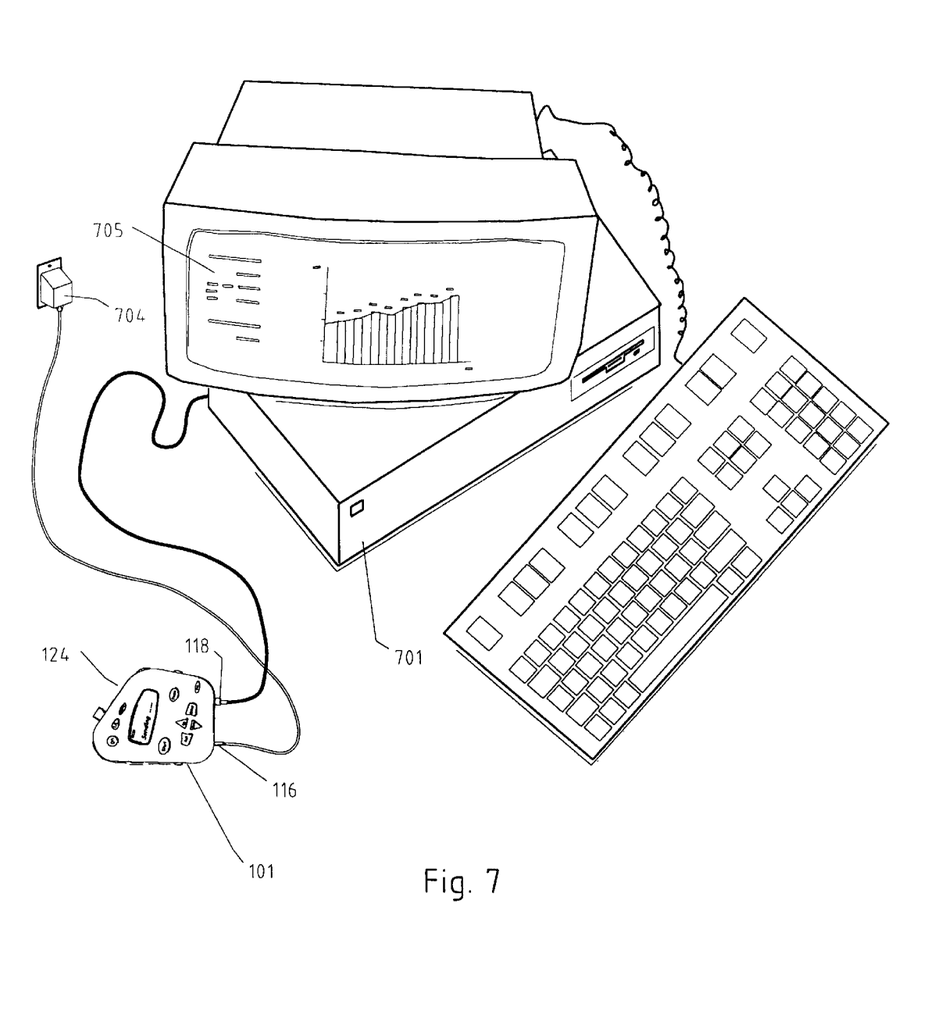
FIG. 7 is a perspective view of a personal computer connected to the GPS-based personal performance monitor and feedback device, displaying a software program for performing long-term historical exercise session data storage, athletic performance trend analysis, and remote configuration of the device.

FIG. 7 is a perspective view of a personal computer 701 connected to the GPS-based personal performance monitor and feedback device 101 via a serial-type port 118. They may also be connected via the infrared-type port 124. By way of example, the computer's monitor screen 705 is shown displaying a customized software program used for athletic performance trend analysis. In addition, this software may be used to facilitate long-term storage of the athlete's personal historical exercise session data and remote configuration of the device. The GPS-based personal performance monitor and feedback device is either powered by its own internal power source 609 or by an external AC/DC transformer 704 plugged into connector 116, as shown.

Figure 8:
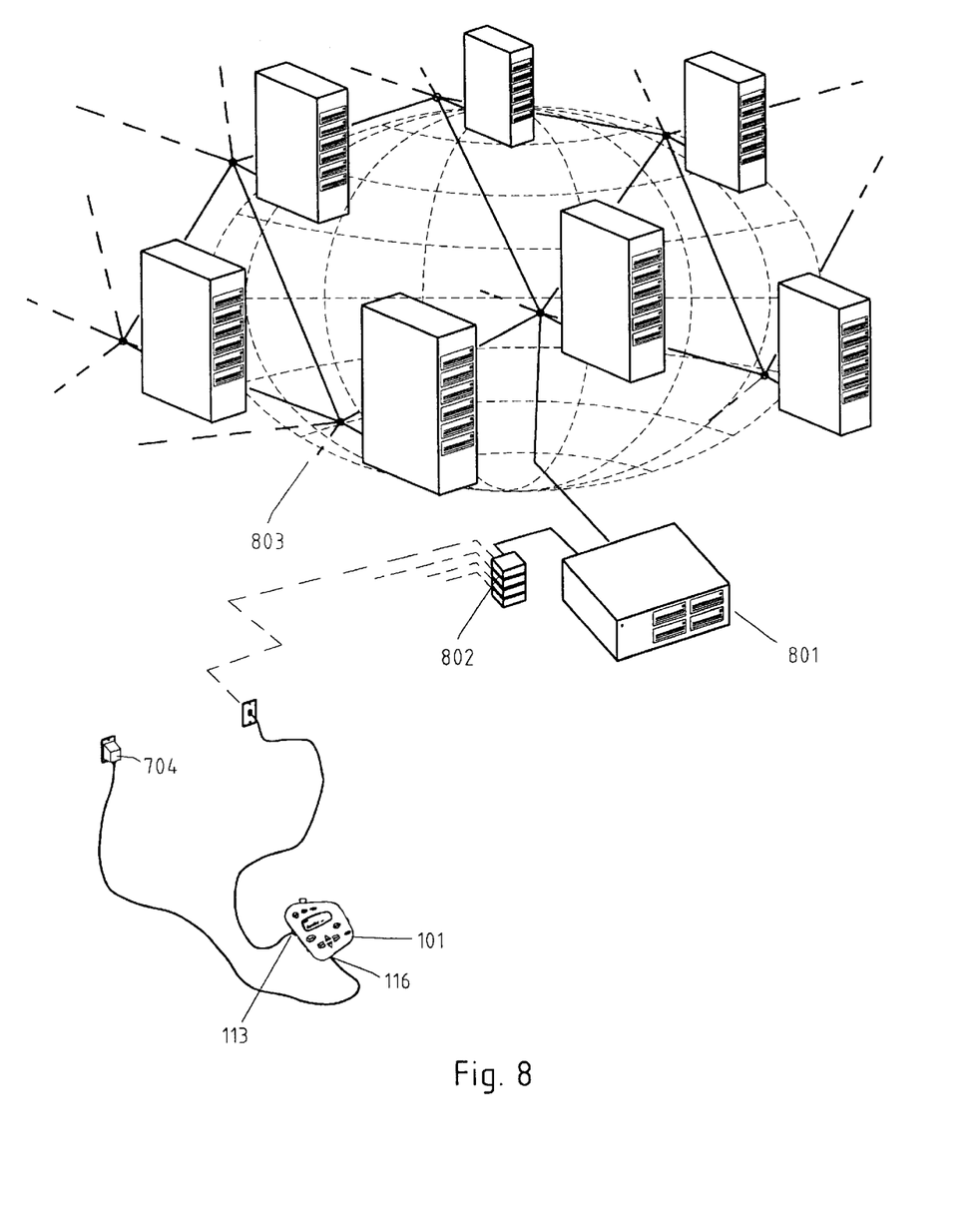
FIG. 8 is a perspective view of the GPS-based personal performance monitor and feedback device connected to a remote computer via an internal modem and a standard telephone line for transferring data.

FIG. 8 is a perspective view of the GPS-based personal performance monitor and feedback device 101 connected to a remote computer 801 and modem bank 802 via its internal modem 613 and a standard telephone line plugged into connector 113. A number of historical exercise session performance data sets (as described below and shown in FIG. 12) can be uploaded to the remote computer 801. The remote computer 801 is connected to the Internet 803. The uploaded data sets are collected, stored, and compiled for presentation on an Internet web site, which compares performances of participating athletes in a variety of ways. Geographically and demographically targeted advertising messages are downloaded to the device 101 from the remote computer 801. The GPS-based personal performance monitor and feedback device 101 is either powered by its own internal power source 609 or by an external AC/DC transformer 704 plugged into connector 116, as shown.

Figure 9:
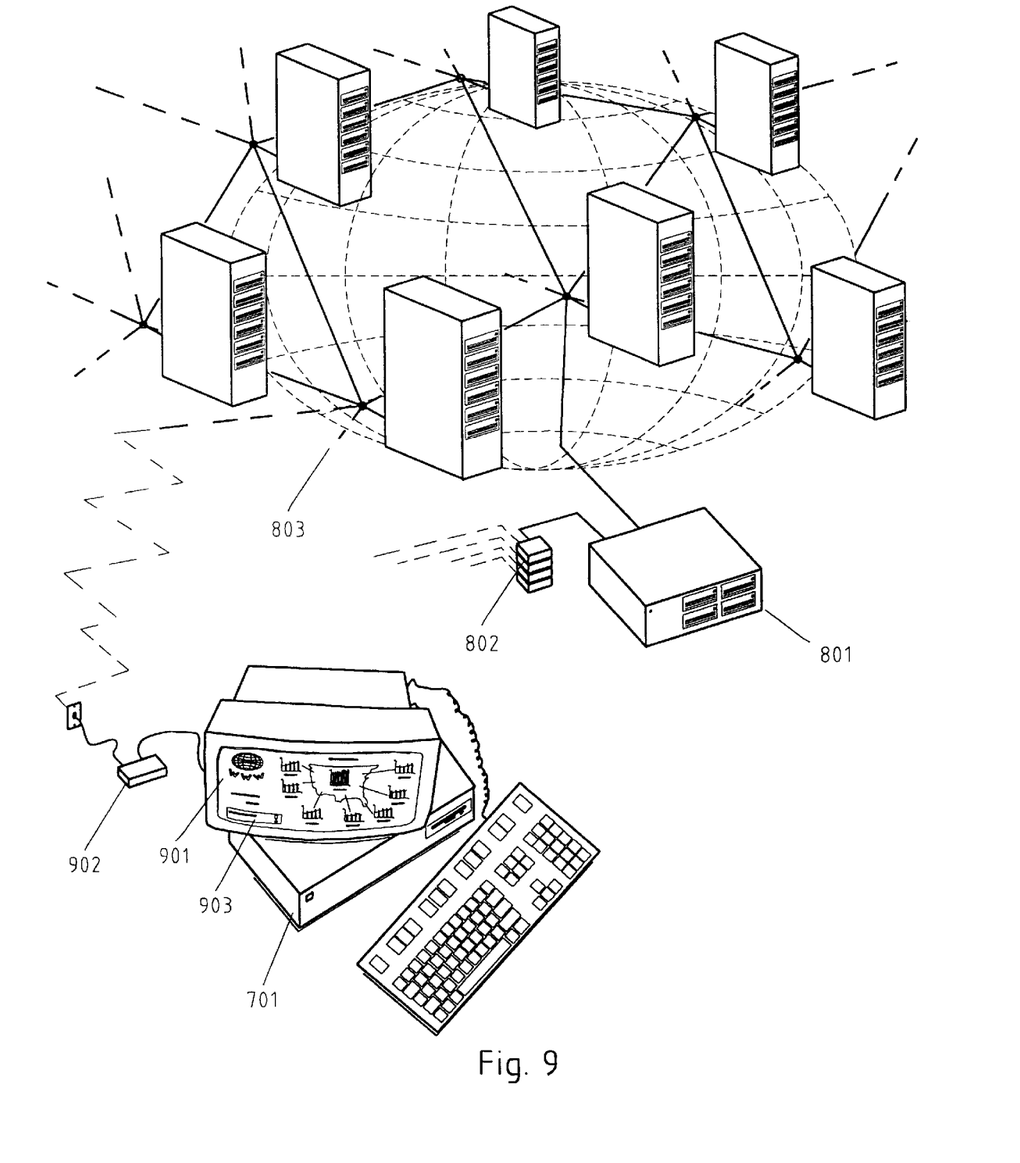
FIG. 9 is a perspective view of a personal computer connected to the Internet, displaying an Internet web page for comparing an athlete's performance to that of other participating athletes.

FIG. 9 is a perspective view of a personal computer 701 connected to the Internet 803. By way of example, the computer 701 is connected via a modem 902 and a standard telephone line. Alternative means of connecting the PC 701 to the Internet 803, such as cable modems, ISDN lines, T1 lines, and so forth, may be used. By way of example, the PC's monitor screen 901 is shown displaying an Internet World Wide Web browser window displaying an Internet web page for comparing an athlete's performance to other participating athletes from around the United States of America. The lower left-hand corner of this computer screen displays an advertising banner 903 specifically designed for and aimed at participating athletes.

Figure 10:
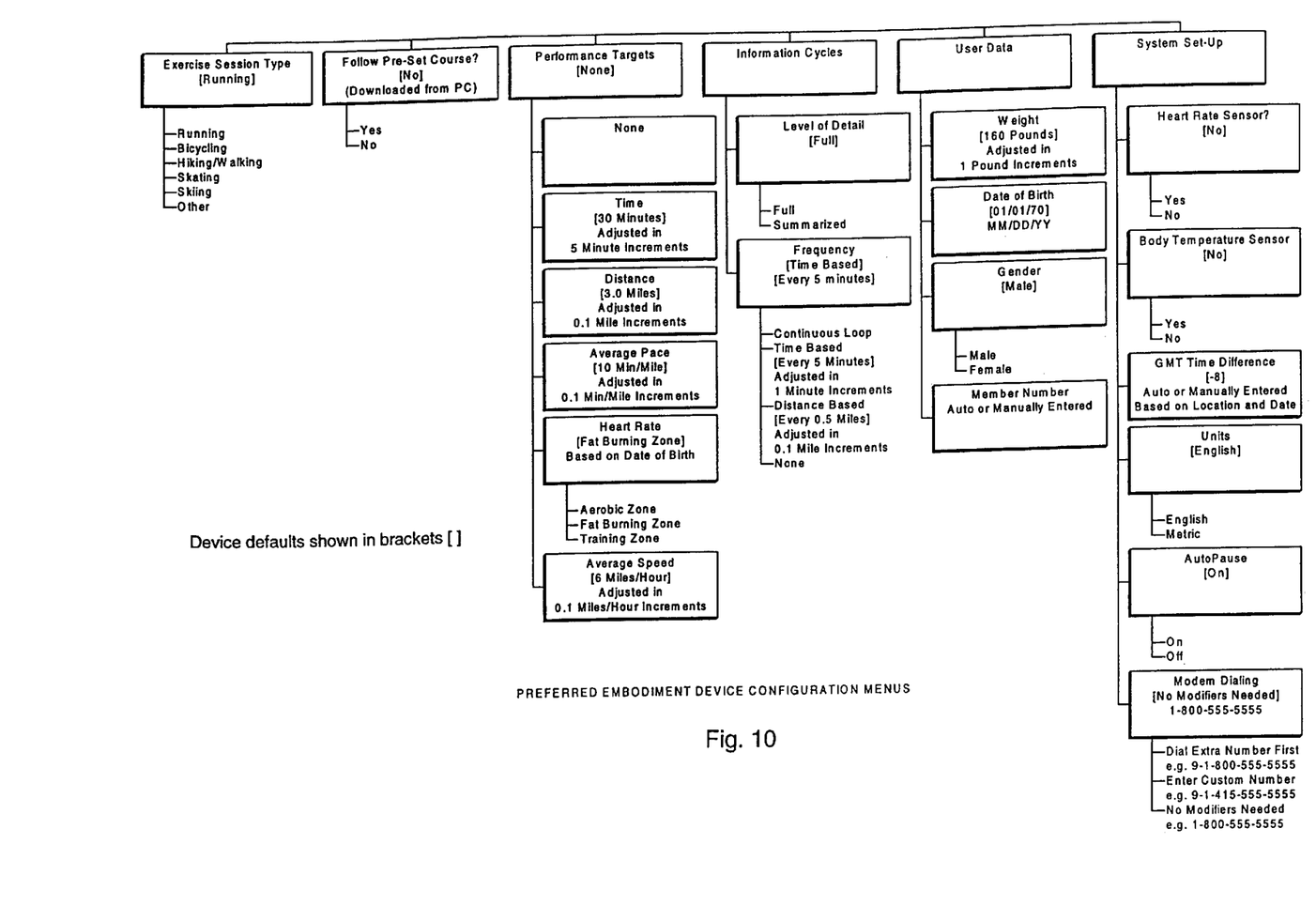
FIG. 10 is a diagram of the menu items used to configure the GPS-based personal performance monitor and feedback device.

FIG. 10 shows device configuration menus of the preferred embodiment. The main menus are designated as "exercise session type", "pre-set course", "performance targets", "information cycles", "user data", and "system set-up". Some of the main menus have sub-menus, which are self-explanatory from the drawing figure. A user can customize his/her exercise session as desired.

Figure 11:
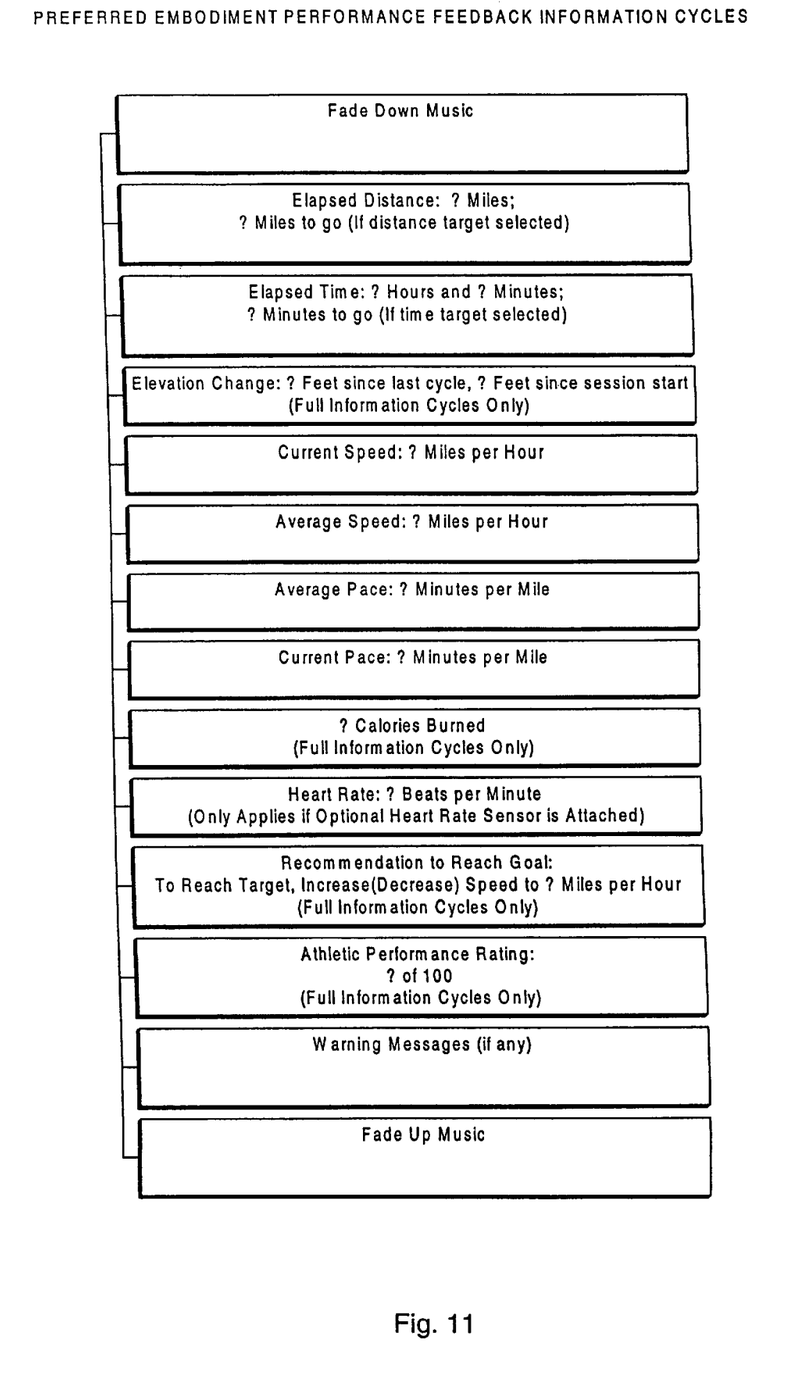
FIG. 11 is a flow chart of the limited and full performance feedback information cycles of the GPS-based personal performance monitor and feedback device.

FIG. 11 is a flowchart showing feedback information cycles of the preferred embodiment. When the music from the AM/FM/TV radio is muted, the menu starts at the top in FIG. 11 and the device scrolls through the different information outputs until the last one (warning messages, if any), and then the music volume is gradually returned to the previous listening level. The operator has full control over the information outputs, and can add or remove different information outputs as desired.

Figure 12:
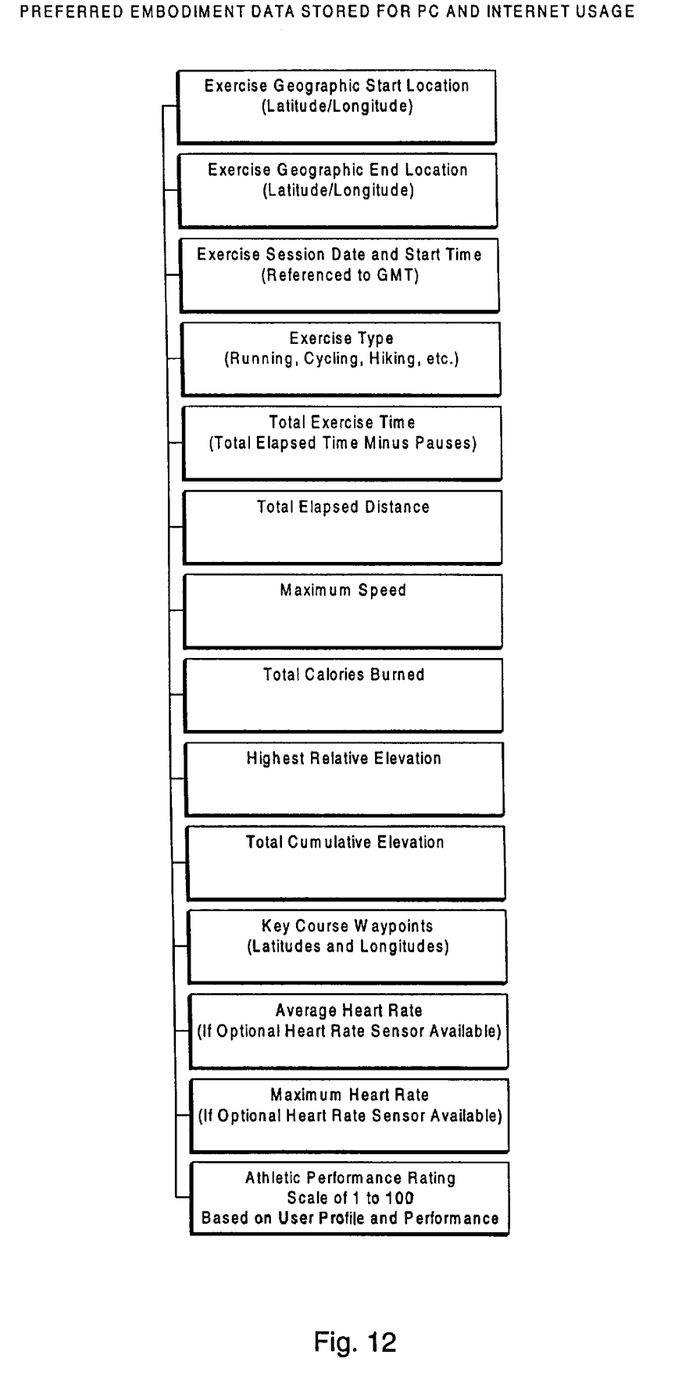
FIG. 12 is a diagram depicting the data stored for personal computer and Internet usage.

FIG. 12 shows the type of data/information that are stored for PC and Internet usage, which are self-explanatory from the drawing figure.

The operation of the device is described below.

Before exercising, the athlete turns on the GPS-based personal performance monitor and feedback device 101 (FIGS. 1A and 1B) and sets his/her preferences using the menu control buttons 115 and display 112. Preference options include, by way of example, performance targets (e.g., total distance, exercise session time, and/or average speed or pace), frequency of feedback information cycles (e.g., continuous, time-related, distance-related, or none), type of feedback information (e.g., full or summarized), and personal data (e.g., gender, birth date, and body weight).

Certain preference options may only need to be set once (such as gender and birth date) or occasionally (such as weight or other variable parameters), while other preference options may be adjusted each time the GPS-based personal performance monitor and feedback device is used. Alternatively, all device settings and user preferences may be set and/or adjusted using a personal computer and an optional software program.

Manufacturer set options may include different display and voice languages, voice gender, and so forth.

After plugging in the set of audio headphones 202 and the GPS receiver antenna 301, the athlete can set his/her favorite radio station(s) and volume and begins his/her stretching and warm-up routine. Once the GPS receiver module 604 confirms by means of the display 112 (FIG. 1A), the LED status indicator 111, and an audible signal that a reliable, geographical position fix is acquired, signaling that the device is properly initialized and ready to go, the athlete can press the start button 103 (FIG. 1A) and commence his/her exercise session. Upon initialization, the device also sets the current atmospheric pressure sensor reading as the reference point from which elevation changes are derived based on changes in atmospheric pressure during the exercise session.

According to well known operations, the GPS receiver 604 receives GPS radio wave signals 205 which are emitted from existing GPS satellites 204 and received via the GPS receiving antenna 301. Currently, a constellation of high altitude GPS satellites 204 are in orbit and available to provide continuous worldwide position fixes in all types of weather conditions. The GPS receiver 604 has a built-in processing unit and memory for processing the GPS radio wave signals 205 to determine the latitude and longitude coordinates of the GPS antenna's current position, as well as determine its current speed and direction of travel.

During the exercise session, the GPS receiver module 604 continuously determines the athlete's geographical position and stores it in the memory 608 along with other information such as the date and time that each position was acquired. From these positions and times, performance data such as elapsed distance, current and average speeds and paces, calories burned, miles remaining, and time remaining are calculated. Based on this data, recommendations to increase or decrease level of effort to meet pre-set performance targets are then determined.

A relative athletic performance rating can also be derived.

A smart algorithm can be used to filter out the erroneous position points resulting from signal interference or from induced errors through the U.S. government's Selective Availability (SA) program, which intentionally limits the absolute accuracy of civilian GPS receivers.

At pre-set intervals, the information is provided to the athlete through the set of audio headphones 202 by means of the audio module 606, during which time the volume of the radio music is temporarily reduced. In addition, by pressing the "Now!" button 105 (FIG. 1B), the pre-set feedback cycle preference is temporarily overridden, the athlete is immediately provided with a current update of his/her performance, and the pre-set feedback cycle preference is resumed. All feedback data is optionally also scrolled across the display 112 while it is being announced via the audio headphones 202.

If the user has downloaded a pre-determined course from his/her PC or an Internet web site, course changes and directional indicators are announced and displayed throughout the exercise session on an as needed basis.

A smart algorithm based on measured parameters such as speed, pace, exercise type, heart rate, and so forth can be optionally used to automatically determine if the athlete has temporarily suspended exercising and temporarily pauses monitoring until exercise is resumed. In addition, monitoring can be manually temporarily suspended by pressing the pause/position button 104 and resumed by pressing the start button 103. A pause condition status indicator is shown on the display 112 during paused operation.

Since the athlete can input pre-set performance targets, any deviation between these targets and the actual measured performance can be determined and conveyed to the athlete. Based on this deviation, the personal performance monitor can also provide the athlete with recommendations for corrections during each feedback cycle. This advice will assist in keeping the athlete on track and, over time, will improve his/her performance.

Other than the "Now!" button 105, the start button 103 and the pause/position button 104, all buttons are made non-operational by pressing the lock/light button 110 for a predetermined period of time, such as 2 seconds. A lock indicator appears in the display 112. In this locked condition, no settings can be accidentally changed. The unit is also unlocked with the lock/light button 110. Normal pressing of the lock/light button 110 (i.e., for a period of time less than the predetermined period) will illuminate the display 112 for a predetermined period of time, such as 5 seconds after the last user input is received.

The display 112 shows the menu options and default settings during the preference set-up before the start of the exercise session. During the exercise, it shows the selected radio band and frequency. It also optionally displays combinations of the GPS initialization status, the quality of the GPS receiver satellite signal reception, the battery life status, the button lock status, the pause condition status, the performance feedback data, course navigational direction indicators, and the device's geographic position. By pressing and holding the pause/position button 104 for at least two seconds, the selected radio band frequency is replaced by the last updated geographical position information (latitude and longitude).

Present day GPS receivers have limited accuracy with respect to altitude. Elevation changes can be determined by measuring changes in the atmospheric pressure. A barometric pressure sensor 610 is used to calculate the relative elevation changes during the exercise session.

The athlete may optionally connect the GPS-based personal performance monitor and feedback device to the personal computer 701 using the serial-type port 118 or the infrared-type port 124 for long term historical exercise session data storage, performance trend analysis, and remote device configuration using customized software.

The athlete may also optionally use the modem 613, connected to the CPU 602, to transmit data from the GPS-based personal performance monitor and feedback device to a remote computer 801 and modem bank 802 via a standard telephone line. This remote computer 801 collects, stores and compiles athletic performance data from participants around the planet. An Internet web site is then used to present performance data from participating athletes.

The inventors envision an Internet web site that would present information such as national and international performance averages for different age/gender groups, virtual competitions, prizes for the most miles run, best average pace, and other performance achievements, personal fitness recommendations, marathon training programs, and so forth. Prior to uploading information for the first time, each participant is assigned a member number by filling out a demographics profile form, either on-line or via mail. Each time the user uploads data, the device relays the user's member number to associate the data with the user.

A smart algorithm (applied by the remote computer 801) based on measured parameters such as average speed and pace, exercise type, average sustained heart rate, elapsed distance and time, and so forth can be optionally used to automatically verify that an exercise session has actually occurred. Verified exercise activity is then used to qualify participants' specific exercise sessions in advertiser-sponsored programs such as product giveaways, earning frequent flier miles, and so forth. This technique may also be used to automatically qualify the results of virtual competitions.

Advertising space on the Internet web site could be sold to athletic companies or other companies which might have athlete's as customers. Geographically and demographically targeted messages could be downloaded to the GPS-based personal performance and feedback device while connected to the remote computer 801. Such messages could be played via the audio module 606 and the audio headphones 202. For example, a runner in San Francisco could be informed about an upcoming race, marathon, a weather report, or even a local shoe sale.

New messages are played once the device has been initialized, the CPU senses that the exercise session has begun by checking for reasonable speed, and the audio volume level is sufficiently high, thus ensuring that the messages are heard by the user. The inventors envision text files being downloaded, but the format may also be direct, compressed, digital audio files such as today's RealAudio files played via Internet web sites. Users may optionally use this feature to learn of athletic events and other interesting messages while travelling. Java or some other software operating system may be embedded in the GPS-based personal performance monitor and feedback device to facilitate this process. Also, a specially developed computer chip designed to efficiently process Java instructions may optionally be incorporated into the device.

The device is initialized at the new destination and connected to the remote computer 801 via the modem 613. The remote computer 801 collects the most recent position information from the device and downloads messages pertaining to the travelling user's new geographic location.

Users may also use the Internet web site to locate other athletes with similar skills and interests to exercise with. For example, a runner travelling to Seattle, Wash. from San Francisco, Calif. could log on to the Internet web site and search for individual runners or groups of runners in the Seattle area with similar skills and interests. An E-mail message can be sent to schedule a future exercise session together. Favorite local courses may also be posted and exchanged via the Internet web site to be optionally used in the GPS-based personal performance monitor and feedback device.

In summary, the GPS-based performance monitor and feedback device of the present invention can be used to provide an outdoor athlete with continuous, consistent, and accurate real-time performance feedback, independent of his/her outdoor location in the world. The data presentation method of using an audio module eliminates the exclusive use of large, power-consuming, cumbersome, and visually distracting displays and leaves the athlete free to concentrate on his/her exercise, safety, and surroundings. It even allows for safely obtaining performance feedback on poorly illuminated tracks and trails. Furthermore, the GPS-based personal performance monitor and feedback device has additional advantages in that it:

provides a motivational tool to the athlete for improving and fine-tuning his/her outdoor performance;

provides the athlete with regularly updated recommendations on how to best achieve his/her pre-set performance targets;

provides the athlete with entertaining music during his/her exercise session, which is reduced in volume during performance feedback cycles;

provides and stores summary data of the most recent exercise achievements, showing progress and trends;

provides the means to upload summary data of each exercise session to a personal computer for permanent storage in an electronic log and further analysis of the user's long term progress and trends;

provides the means to remotely configure the device;

provides a total health monitor when optional sensors such as a heart rate sensor or body temperature sensor are added;

provides a direction indicator to guide the athlete through a course based on downloaded geographical waypoints;

provides the means to upload summary data of each exercise session to an Internet web site via a remote computer for comparing the performance of participants from around the globe;

provides the means for athletes to locate other athletes with similar skills and interests;

provides the means for athletes to exchange favorite course waypoints via the Internet;

provides the means to stage virtual competitions between participating athletes from around the world;

provides the means to verify that a legitimate exercise session has actually taken place;

provides the means for advertisers to present geographically and demographically targeted messages to highly well-defined potential customers via the world wide web;

provides the means for athletes to earn products and services from sponsors for their efforts;

provides the means for advertisers to directly distribute geographically and demographically targeted messages to participating athletes;

provides a means for advertisers to ensure that their messages are actually heard; and provides the means for scientists and medical researchers to accurately and consistently monitor a group of individuals and study the long term relationship between exercise and health.

The attached drawing figures are illustrative only, and the GPS-based personal performance monitor and feedback device of the present invention can be provided in various shapes, forms and configurations.

Although the description above is of the preferred embodiments, it should not be construed as limiting the scope of the invention. For example, the case 601 may have a different shape and look, or even be completely integrated into the set of audio headphones, together with the GPS receiver antenna 301 or the audio headphones 202 can be replaced by a simple speaker integrated in the case 601.

While this invention has been disclosed in connection with a particular example thereof, no limitation is intended thereby except as defined in the following claims. Various modifications could be made without departing from the spirit and scope of this invention.

We claim:

1. A portable feedback system providing regular updates on an athlete's performance, comprising:
    a global positioning system GPS receiver that obtains a series of time-stamped waypoints;
    means for computing athletic performance feedback data from the series of time-stamped waypoints obtained by said GPS receiver; and
    means for presenting the athletic performance feedback data to an athlete.

2. A portable feedback system as recited in claim 1, further comprising a radio, integrated with said GPS receiver.

3. A portable feedback system as recited in claim 1, wherein said means for presenting comprises a voice chip.

4. A portable feedback system as recited in claim 1, wherein said means for presenting comprises digital audio files.

5. A portable feedback system as recited in claim 1, wherein said means for presenting comprises a voice chip and digital audio files.

6. A portable feedback system as recited in claim 1, further comprising means for connecting said means for computing to an external computer.

7. A portable feedback system as recited in claim 1, further comprising means for suspending and resuming operation of said means for computing when a speed of the athlete falls below a predetermined threshold.

8. A portable personal performance monitor comprising a global positioning system GPS unit for acquiring time-stamped geographical position data of an athlete and converting said position data into athletic performance feedback data, and a radio with an audio headset, said GPS unit and said radio being integrated into a single unit, and means for presenting the athletic performance feedback data over said audio headset.

9. A portable personal performance monitor as recited in claim 8, further comprising means for muting said radio when the athletic performance feedback data is presented over said audio headset.

10. A portable personal performance monitor as recited in claim 8, wherein said GPS unit comprises an external antenna mounted on said audio headset.

11. A portable personal performance monitor as recited in claim 8, wherein said GPS unit comprises an external antenna, and further comprising a baseball cap to which said external antenna is attached.

12. A portable personal performance monitor as recited in claim 8, wherein said single unit comprises a housing having a plurality of buttons for operating said GPS unit and said radio.

13. A portable personal performance monitor as recited in claim 12, wherein said buttons comprise:
    a start button for starting and resuming data collection;
    a pause button for suspending data collection; and
    another button for obtaining immediate athletic performance updates from said GPS unit.

14. A portable personal performance monitor as recited in claim 8, further comprising a memory storage device and a central processing unit for controlling operation of said GPS unit.

15. A portable personal performance monitor as recited in claim 14, further comprising a sensor for sensing atmospheric pressure, an output of said sensor being input to said central processing unit.

16. A portable personal performance monitor as recited in claim 14, further comprising a modem connected to said central processing unit for transmitting information to and from said central processing unit.

17. A portable personal performance monitor as recited in claim 8, further comprising an electrical connector for connecting the monitor to a personal computer.

18. A portable personal performance monitor as recited in claim 8, further comprising an infrared port for connecting the monitor to a personal computer.

19. A portable personal performance monitor as recited in claim 14, further comprising a heart rate sensor for sensing a heart rate of the athlete, an output of said heart rate sensor being input to said central processing unit.

20. A portable personal performance monitor as recited in claim 14, further comprising a body temperature sensor for sensing a body temperature of the athlete, an output of said body temperature sensor being input to said central processing unit.

21. A system for comparing the performance of an athlete with the performance of other athletes, said system comprising:
    a global positioning system GPS receiver for obtaining a series of time-stamped waypoints;
    means for computing athletic performance feedback data from the series of time-stamped waypoints obtained by said GPS receiver;
    means for presenting the athletic performance feedback data to an athlete; and
    a modem for transmitting the athletic performance feedback data to a remote computer for comparison with athletic performance data of other athletes.

22. A system as recited in claim 21, further comprising means for verifying actual exercise activity.

23. A system as recited in claim 21, further comprising a headset and an audio module for presenting the athletic performance feedback data over said headset.

24. A system as recited in claim 21, further comprising an Internet web site adapted to receive the athletic performance feedback data and display comparison data representing relative performance of two or more athletes.

25. A system as recited in claim 24, further comprising means for exchanging GPS route waypoints via said Internet web site.

26. A system as recited in claim 24, wherein said Internet web site is adapted to display customized individual training advice.

27. A system as recited in claim 24, wherein said Internet web site is adapted to facilitate virtual athletic competitions.

28. A system as recited in claim 24, wherein said Internet web site is adapted to display advertisements.

29. A system as recited in claim 23, wherein said system is adapted to receive and present advertising messages.

30. A system as recited in claim 29, further comprising means for sensing a volume level to ensure that the advertising messages are heard.

31. A portable personal performance monitor for an athlete, comprising:
    a housing, said housing storing;
        a central processor unit,
        a memory storage device,
        a global positioning system GPS unit connected to said central processor unit, a radio connected to said central processor unit, means for generating audible information connected to said central processor unit, means for inputting control information into said central processor unit, and means for displaying information output from said central processor unit;

a GPS antenna connected to said GPS unit;

a radio antenna connected to said radio receiver; and headphones connected to said means for generating audible information and said radio receiver via said central processor unit.

32. A portable personal performance monitor as recited in claim 31, further comprising:

a heart rate monitor connected to said central processor unit.

33. A portable personal performance monitor as recited in claim 31, further comprising:

a body temperature sensor connected to said central processor unit.

34. A portable personal performance monitor as recited in claim 31, further comprising:

a sensor for sensing atmospheric pressure, an output of said sensor being input to said central processor unit.

35. A portable personal performance monitor as recited in claim 31, wherein said housing also stores a modem connected to said central processor unit.

36. A portable personal performance monitor as recited in claim 31, wherein said housing has an electrical connector for connecting said central processor unit to an external personal computer.

37. A portable personal performance monitor as recited in claim 31, wherein said housing has an infrared port for connecting said central processor unit to an external personal computer.

38. A portable health monitoring and analysis system, comprising:

a global positioning system GPS receiver for obtaining a series of time-stamped waypoints;

means for computing performance feedback data from the series of time-stamped waypoints obtained by said GPS receiver; and means for storing the performance feedback data and presenting the performance feedback data for health monitoring and analysis.

\* \* \* \* \*